(12) United States Patent
Brunner et al.

(10) Patent No.: US 10,605,677 B2
(45) Date of Patent: Mar. 31, 2020

(54) METHOD FOR CALIBRATING A TEMPERATURE CONTROL IN THERMAL ANALYSES OF SAMPLES

(71) Applicant: Netzsch-Gerätebau GmbH, Selb (DE)

(72) Inventors: Martin Brunner, Konradsreuth (DE); André Lindemann, Merseburg (DE)

(73) Assignee: Netzsch-Gerätebau GmbH, Selb (DE)

( * ) Notice: Subject to any disclaimer, the term of this patent is extended or adjusted under 35 U.S.C. 154(b) by 302 days.

(21) Appl. No.: 15/684,550

(22) Filed: Aug. 23, 2017

(65) Prior Publication Data
US 2018/0080837 A1    Mar. 22, 2018

(30) Foreign Application Priority Data
Sep. 21, 2016  (DE) .......................... 10 2016 117 754

(51) Int. Cl.
| | | |
|---|---|---|
| G01K 15/00 | (2006.01) | |
| G01N 25/48 | (2006.01) | |
| G01J 5/08 | (2006.01) | |
| G01J 5/10 | (2006.01) | |

(Continued)

(52) U.S. Cl.
CPC .......... G01K 15/005 (2013.01); G01J 5/0896 (2013.01); G01J 5/10 (2013.01); G01K 7/021 (2013.01); G01N 25/482 (2013.01); *G01N 25/04* (2013.01)

(58) Field of Classification Search
CPC .......... G01J 5/00; G01J 3/42; G01N 25/4833; G01N 2291/02881; G01N 25/4866; G01N 21/274; G01N 21/95607; G01N 25/482; G01N 29/024; G01N 21/171; G01N 21/314; G01N 15/06; G01N 2015/0693; G01N 2021/451; G01N 21/01; G01K 13/00
USPC ..... 374/121, 124, 130, 161, 2, 1, 20–39, 45, 374/129
See application file for complete search history.

(56) References Cited

U.S. PATENT DOCUMENTS 3,531,211 A * 9/1970 Staunton ............ G01N 21/0303
356/244
3,987,303 A * 10/1976 Stoft .................. G01N 21/3504
250/343

(Continued)

FOREIGN PATENT DOCUMENTS

DE        19907804 C1     3/2000
DE     102007005618 A1    8/2008
(Continued)

*Primary Examiner* — Gail Kaplan Verbitsky
(74) *Attorney, Agent, or Firm* — Whitmyer IP Group LLC (57) ABSTRACT

A method for calibrating thermal analysis device includes: photothermal measurements on a sample consecutively held in the plurality of sample holders, or on a plurality of similar samples, which are in each case held in one of the plurality of sample holders, wherein a first side of the respective sample is irradiated with an electromagnetic excitation pulse and a thermal radiation emitted by a second side of this sample is captured; comparing results of the photothermal measurements for the plurality of sample holders; in each case determining at least one correction parameter for each sample holder based on a result of the comparison; and calibrating the temperature measuring system of the device and/or the temperature control systems of the device based on the determined correction parameters.

14 Claims, 3 Drawing Sheets

(51) Int. Cl.
*G01K 7/02* (2006.01)
*G01N 25/04* (2006.01)

(56) References Cited

U.S. PATENT DOCUMENTS

| | | | | |
|---|---|---|---|---|
| 4,537,510 | A | * | 8/1985 | Takahasi .................. G01J 1/16 |
| | | | | 250/214 AG |
| 5,529,755 | A | * | 6/1996 | Higashio ............ A61B 5/14532 |
| | | | | 422/82.09 |
| 5,672,875 | A | * | 9/1997 | Block .................. A61B 5/0059 |
| | | | | 250/343 |
| 6,530,686 | B1 | * | 3/2003 | Nakamura ......... G01N 25/4826 |
| | | | | 219/494 |
| 2004/0021861 | A1 | * | 2/2004 | Lewis ....................... G01J 3/02 |
| | | | | 356/326 |
| 2008/0123099 | A1 | * | 5/2008 | Takahashi ............ G01N 21/171 |
| | | | | 356/450 |
| 2009/0034579 | A1 | * | 2/2009 | Schick .................. G01K 17/00 |
| | | | | 374/10 |
| 2017/0030827 | A1 | * | 2/2017 | Nickel ................... G01N 21/01 |
| 2019/0195781 | A1 | * | 6/2019 | Waclawek ........... G01N 21/171 |

FOREIGN PATENT DOCUMENTS

| | | | |
|---|---|---|---|
| DE | 102012106955 A1 | | 2/2014 |
| EP | 083761 A1 | * | 7/1983 |
| EP | 3051278 A1 | | 8/2016 |
| RU | 2075062 C1 | * | 3/1997 |

\* cited by examiner

METHOD FOR CALIBRATING A TEMPERATURE CONTROL IN THERMAL ANALYSES OF SAMPLES

TECHNICAL FIELD

The invention at hand relates to a method for calibrating a device for the thermal analysis of samples according to the present invention.

BACKGROUND

In the thermal analysis, properties of a material are examined by means of a sample from the respective material as a function of the temperature. A correct thermometry, i.e. a correct measurement of the temperature of the sample, plays an important role hereby.

Temperature sensors in the form of thermocouples or electrical resistance thermometers, e.g., which can be arranged in thermal contact to the sample, e.g., in order to measure the temperature of a sample during the examination thereof, are known from the prior art of devices for the thermal analysis of samples.

This measurement, however, may be more or less error prone, for instance because such a temperature sensor does not measure the temperature in the interior of the sample, but, e.g. at an edge of the sample. This measuring error is even more significant for temperature sensors, which are frequently used and which cannot be arranged in direct contact to the sample, but which are instead arranged adjacent to the sample, thus spatially separated therefrom, inside a sample chamber of the device.

This problem can be reduced significantly by means of a suitable "calibration" of the used temperature sensor or the temperature measuring system formed therewith, respectively. Calibration means that one or a plurality of correction parameters are determined and stored, in order to be able to consider them accordingly in response to subsequent thermal analyses.

For such a calibration, it can be provided, e.g., to measure the temperature of one or a plurality of samples, which are each to be melted at known temperatures, in the respective device for the thermal analysis during the course of a temperature program (predetermined temporal change of the sample temperature), in order to then use a comparison of the melting temperatures measured by means of the temperature measuring system with the melting temperatures, which are known, e.g. from the literature, to calibrate the temperature measuring system.

A sample comprising a known Curie temperature, e.g., can also be used as an alternative to the use of such a melting standard for the calibration.

Devices for the thermal analysis, in the case of which such a calibration of the temperature measuring system can be carried out, e.g. in the above-described manner, are known from the prior art in a variety of designs. One example for this is the device LFA 467 HT HyperFlash" by Netzsch-Gerätebau GmbH, Selb, Germany. This known device comprises:

a sample chamber comprising a plurality of sample holders, which are in each case embodied to hold a sample,
for each of the plurality of sample holders, a controllable temperature control system (here: "mini tube furnace") assigned to said sample holder, for controlling the temperature of the sample held by this sample holder,
a temperature measuring system (here: comprising a plurality of thermocouples in each case assigned to one of the sample holders) for measuring the temperature of the samples,
a photothermal measuring system for irradiating a first side of the samples comprising an electromagnetic excitation pulse and for capturing a thermal radiation emitted by a second side of the samples located opposite the first side as a result of the excitation pulse,
a control and evaluating system for controlling the temperature control systems and the photothermal measuring system and for recording measuring data, which represent at least one physical property of the samples (here: temperature conductivity and/or specific thermal capacity), which differs from the temperature of the samples, as a function of the temperature of the samples.

A disadvantage of the known generic calibrating methods is, for example, the effort associated therewith and the limitation to very specific "calibrating temperatures" (in the case of which a melting or another easily detectable phase conversion, respectively, takes place).

When the calibration is to take place across a relatively large temperature range, this is made more difficult in that calibration measurements must in each case be carried out repeatedly with different samples, which serve as standard, for each individual sample holder (each "sample or measuring position", respectively). The different phase conversion temperatures of these samples then provide a corresponding plurality of "support locations" (calibrating temperatures) relating to the respective temperature range.

In addition, possible chemical material reactions must always be observed as well, which is why for example a cobalt standard sample (comprising a known Curie temperature of approx. 1115° C.) cannot be used in a siliceous sample holder (e.g. of SiC), because the cobalt reacts with silicon at higher temperatures.

Based on a calibrating method of the above-discussed type, it is an object of the invention at hand to overcome the disadvantages thereof and to specify an alternative calibrating method.

The method according to the invention for calibrating a device for the thermal analysis of the above-mentioned type comprises the following steps:

carrying out photothermal measurements by means of the photothermal measuring system
on a certain sample, which is consecutively held in the plurality of sample holders for this purpose and which is in each case subjected to a photothermal measurement, or
on a plurality of similar samples, which are in each case held in one of the plurality of sample holders for this purpose and which are in each case subjected to a photothermal measurement,
wherein in the case of the photothermal measurements, a first side of the respective sample is in each case irradiated with an electromagnetic excitation pulse and a thermal radiation emitted by a second side of this sample located opposite the first side is captured as a result of the excitation pulse,
comparing results of the photothermal measurements for the plurality of sample holders,
in each case determining at least one correction parameter for each sample holder based on a result of the comparison, calibrating the temperature measuring system and/or the temperature control systems based on the determined correction parameters.

The basic idea of the invention is to use the photothermal measuring system, which is already present in a respective device, for initially carrying out a photothermal measurement (of the type provided according to the invention) for each of the plurality of sample holders or synonymously the plurality of "sample positions", respectively, wherein it would "normally" be expected on the basis of the use of a certain sample or a plurality of similar samples that the measurements provide identical results, in order to then use differences of the results, which do in fact appear in practice, to determine correction parameters for the individual sample holders or sample positions, respectively, so as to finally calibrate the temperature measuring system and/or the temperature control systems of the device on the basis of the determined correction parameters.

In a particularly advantageous embodiment of the calibrating method, the above-mentioned method steps are carried out, after a calibration of the temperature measuring system (and/or of the temperature control system), which is as accurate as possible, with regard to the temperature measurement (or temperature control, respectively) had already been carried out beforehand for (at least) one sample holder or (at least) one sample position, respectively, in any suitable manner for this sample position (e.g. by means of a melting standard or the like). The above-mentioned method steps then provide for a calibration of the temperature measuring system, which can be carried out very easily by means of the correction parameters, with regard to the temperature measurement of the remaining sample positions.

SUMMARY

According to the invention, provision can also be made as an alternative or in addition to a calibration of the temperature measuring system for a calibration of the plurality of temperature control systems, which are in each case assigned to one of the sample holders. The background is as follows:

In response to the thermal analysis, the temperature of all samples are to be controlled as evenly as possible by means of the temperature control systems (identical sample temperatures) and this "common" sample temperature is to be captured as exactly as possible by means of the temperature measuring system.

While "calibrating the temperature measuring system" means that one or a plurality of correction parameters are determined and stored in order to be able to consider them in response to subsequent thermal analyses for a more exact capturing of the sample temperature, "calibrating the temperature control systems" means that one or a plurality of correction parameters are determined and stored in order to be able to consider them in response to subsequent thermal analyses for evenly controlling the temperature of the samples.

While correction parameters determined for calibrating the temperature measuring system accordingly determine or modify (correct), respectively, a conversion of temperature sensor signals into a "captured sample temperature", correction parameters determined for calibrating the temperature control systems serve the purpose of determining the relationship of the individual heating power (or cooling power, respectively) effected by means of the individual temperature control systems, relative to one another or of modifying (correcting), respectively.

In one embodiment, the temperature measuring system has a temperature sensor, which is arranged in the sample chamber and which is shared by the plurality of sample holders. As an alternative or in addition, the temperature measuring system has a temperature measuring sensor, which is in each case arranged in the sample chamber and is assigned to the respective sample holder (or to the corresponding "sample position", respectively), for each of the sample holders.

When the temperature measuring system only has one temperature sensor shared by all sample holders, it is clear that the "common sample temperature", e.g., which has already been mentioned, can be measured therewith (whereby at least one correction parameter can be considered in response to the concrete conversion of the temperature sensor signal into the "captured common sample temperature").

When the temperature measuring system, however (as an alternative or in addition) in each case has an individual temperature measuring sensor, i.e. which is assigned to the respective sample holder, for each of the sample holders, more detailed information can advantageously be obtained in response to the capturing of the temperature (namely with regard to unwanted temperature differences between the individual sample holders or sample positions respectively). However, the mentioned "common sample temperature", e.g., can also be captured in this case, for instance by means of averaging the results of the individual temperature measurements. In the alternative, for instance when a certain irregularity of the temperature control of the plurality of samples is accepted, the results of the individual temperature measurements can be considered when recording the measuring data as individual (different, if applicable) individual temperatures for the individual samples.

As mentioned, the use of the calibrating method for a device, in the case of which the temperature measuring system only has a (single) temperature sensor, which is shared by the plurality of sample holders, e.g., also lies within the scope of the invention. When assuming that this temperature sensor "correctly" specifies the temperature of a sample located in a "first sample holder" (e.g. due to a prior calibration for a "first sample position"), whereas it is initially unknown, whether the temperature sensor also correctly specifies the temperature of a sample located in a "second sample holder' (or in even further sample holders), the execution of photothermal measurements provided according to the invention for these two sample positions (and, if applicable, for further sample positions), can uncover a corresponding actual temperature difference, namely when the two or even further photothermal measurements, respectively, provide different results.

Based on the determined correction parameters, the temperature measuring system, e.g., can be corrected in this case with regard to the temperature capturing for the second sample holder (and analogously for further sample holders) and/or the control (e.g. heating current setting) for the temperature control system, which is assigned to the second sample holder, can be corrected in such a way that the temperature prevailing there corresponds more accurately to the temperature, which prevails at the first sample holder.

In one embodiment, the device further comprises a controllable sample changing system, by means of which each of the sample holders can be brought into a relative position, which is suitable for a photothermal measurement on a sample held therein, with regard to the photothermal measuring system. One and the same photothermal measuring system can thus advantageously be used for each of the plurality of sample holders.

In one embodiment, every temperature control system has an electrically operable heating jacket, which is arranged on the assigned sample holder.

In one embodiment, the control and evaluating system is embodied to carry out the following steps for carrying out the calibrating method:
- optional: controlling a sample changing system of the device, in order to consecutively bring each of the sample holders into a relative position, which is suitable for a photothermal measurement on a sample held therein, with regard to the photothermal measuring system,
- for each of the plurality of photothermal measurements:
- controlling the respective temperature control system for setting a predetermined temperature of the respective sample and controlling the photothermal measuring system for irradiating the first side of the sample with a predetermined electromagnetic excitation pulse,
- measuring the temperature of the sample by means of the temperature measuring system and
- recording measuring data, which represent a time-dependent course of the thermal radiation emitted by the second side of the sample,
- comparing results of the photothermal measurements for the plurality of sample holders,
- in each case determining at least one correction parameter for each sample holder, based on a result of the comparison,
- calibrating the temperature measuring system and/or the temperature control systems, based on the determined correction parameters.

In one embodiment, the comparing of the results of the photothermal measurements comprises a comparison of the respective maximum values reached in the time-dependent course of the emitted thermal radiation.

BRIEF DESCRIPTION OF THE DRAWINGS

The invention will be described in more detail below by means of exemplary embodiments with reference to the enclosed drawings.

DETAILED DESCRIPTION

Figure 1:
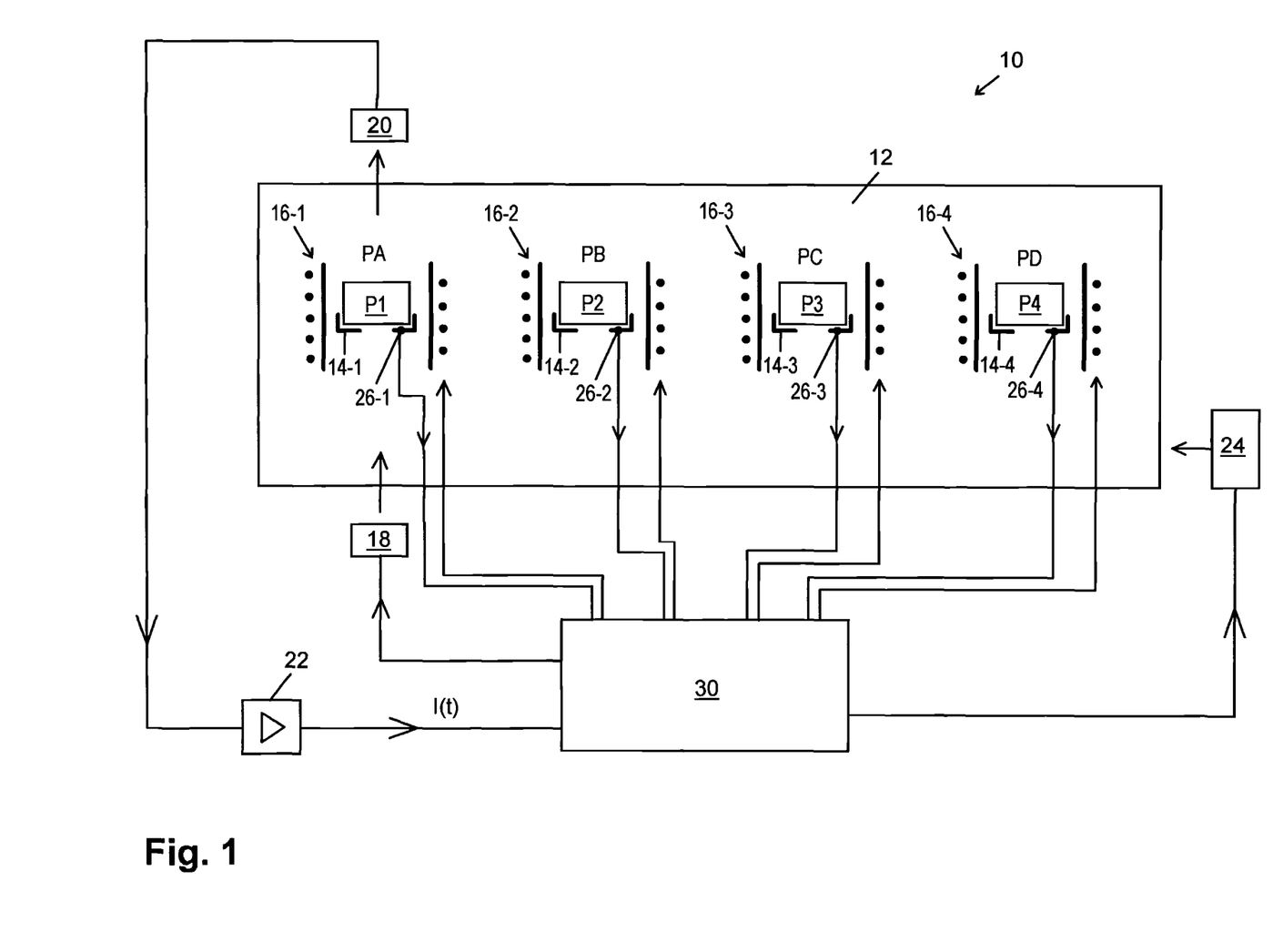
FIG. 1 shows a device for the thermal analysis of samples according to an exemplary embodiment.

Schematically, FIG. 1 shows a device 10 for the thermal analysis of samples.

The device 10 comprises a sample chamber 12 comprising a plurality of (here four) sample holders 14-1, 14-2, 14-3 and 14-4, which are in each case embodied for holding a sample.

The provision of a plurality of sample holders makes it possible in an advantageous manner to simultaneously control the temperature and examine a plurality of samples, which represents a significant time savings in practice. Four samples P1, P2, P3 and P4, which are in each case positioned on one of the sample holders 14-1 to 14-4 and which can thus be subjected to the thermal analysis provided by the device 10, e.g. during the course of a single "temperature program", are illustrated in an exemplary manner in FIG. 1.

The determination of a time-dependent sequence of a temperature in the interior of the sample chamber 12 and thus of the temperature of the samples (in FIG. 1: P1 to P4) is to hereby be understood as temperature program.

A temperature program, in the case of which the interior of the sample chamber 12 is increased step-by-step starting at a start temperature to an end temperature, is often preferred, wherein the samples are examined with respect to at least one physical property, which differs from the temperature of the sample, in order to record corresponding measuring data (as a function of the sample temperature), after each temperature step by keeping the (ideally identical) temperature constant.

It turned out to be advantageous in particular for realizing a temperature program comprising a step-by-step change of the sample temperature, when for each of the plurality of sample holders 14-1 to 14-4 an individual controllable temperature control system 16-1, 16-2, 16-3 or 16-4, respectively, i.e. which is assigned to said sample holder, is provided for controlling the temperature of the sample, which is held by the respective sample holder. Advantageously, this reduces the "thermal inertia", so that a change can be made relatively quickly during the course of the temperature program from a target temperature to another target temperature, which, in turn, represents a significant time savings in practice.

As symbolized in FIG. 1, the temperature control systems 16-1 to 16-4 can in each case have an electrically operable heating jacket, which is arranged on the assigned sample holder 14-1, 14-2, 14-3 or 14-4, respectively, or which surrounds the respective sample P1, P2, P3 or P4, respectively, held thereby.

The positions of the plurality of samples, in the illustrated example four samples P1 to P4 on the sample holders 14-1 to 14-4, will hereinafter also be identified as "sample positions" PA, PB, PC and PD.

It goes without saying that in response to a simultaneous temperature control of the samples P1 to P4, the temperature in the interior of the sample chamber 12 should be as even as possible, or at least the temperatures, which prevail directly at the sample positions PA, PB, PC and PD, should be identical, if possible, respectively. For this purpose, the sample holders 14-1 to 14-4 as well as the assigned controllable temperature control systems 16-1 to 16-4 thereof are embodied completely identical and are furthermore arranged as symmetrically as possible (e.g. distributed equidistantly on a circumference in the center of the sample chamber 12), wherein the individual temperature control systems 16-1 to 16-4 are controlled substantially similarly (e.g. with the same electrical heating current). "In the ideal case", the temperatures at the sample positions PA to PD should be completely identical in this respect.

It turned out, however, that such a "balancing of the temperature control" does not always meet the demands in practice, in particular with regard to carrying out thermal analyses with highly accurate temperature capturing and/or very even temperature control of all samples (identical sample temperatures).

Against this background, provision is made for a special method for calibrating the temperature capturing and/or the temperature control (according to a heating or cooling power, respectively, of the individual temperature control systems), which will be explained in more detail below, is provided for the illustrated device 10.

With regard to the "thermal analysis" of the respective samples (e.g. the illustrated samples P1 to P4), which can be carried out by means of the device 10, provision is made here for a "photothermal measuring system" comprising an excitation source, here a laser 18, and for a detector, here an infrared detector 20 in FIG. 1 in an exemplary manner. The excitation source or the laser 18, respectively, serves to irradiate a first side of a respective sample with an electromagnetic excitation pulse, and the detector 20, here in connection with a signal amplifier 22 arranged downstream, serves to capture a thermal radiation emitted by a second side of the respective sample located opposite the first side as a result of the excitation pulse. Temperature conductivity and/or specific thermal capacity of the samples, e.g., can thus be analyzed in a manner, which is known per se.

In the illustrated example, the device 10 is equipped with a controllable sample changing system, which is symbolized at 24, by means of which one of the sample holders 14-1 to 14-4 can in each case be brought into a light path (provided in a stationary manner here) of the photothermal measuring system (18, 20). In the situation illustrated in FIG. 1, the first sample P1 is located in the light path of the photothermal measuring system.

Such sample changing systems are known from the prior art and thus do not need to be discussed in detail here. It can be a motor-driven "revolver", in the case of which one of the sample holders 14-1 to 14-4 can be turned into the light path of the photothermal measuring system, depending on the controlled turning position.

The device 10 further comprises a temperature measuring system for measuring the temperature of the samples on the sample holders 14-1 to 14-4. In the illustrated example, this temperature measuring system in each case has a temperature measuring sensor 26-1, 26-2, 26-3 or 26-4, respectively, which is arranged in the immediate vicinity of the corresponding sample position PA, PB, PC or PD, respectively, and which is thus assigned to the respective sample holder 14-1, 14-2, 14-3 or 14-4, respectively.

In the alternative or in addition, the temperature measuring system can also have a temperature sensor, which is arranged in the sample chamber 12 and which is shared by the plurality of sample holders 14-1 to 14-4.

Finally, the device 10 comprises a control and evaluating system 30 for controlling the temperature control systems 16-1 to 16-4 and the photothermal measuring system and for recording measuring data, as already mentioned, which represent at least one physical property of the samples, which differs from the temperature of the samples, as a function of the temperature of the samples (here, e.g., temperature-dependent temperature conductivity of the samples P1 to P4).

In addition to the photothermal measuring system, further measuring systems could also be comprised by the device 10, e.g. a weighing system for weighing the samples, or a force measuring system for measuring a force exerted by the samples (e.g. based on thermal expansion), a length measuring system for measuring a change in dimension carried out by the samples (e.g. based on thermal expansion), etc. However, only the mentioned photothermal measuring system is necessary to realize the invention.

In the illustrated example, the control and evaluating system 30 is further embodied for controlling the sample changing system 24, e.g. for bringing each of the sample holders 14-1 to 14-4 into a relative position, which is suitable for a photothermal measurement on a sample held therein, with respect to the photothermal measuring system, during the course of a measuring program for the consecutive thermal analysis of the plurality of samples P1 to P4.

After an equipping of the device with the respective samples, e.g. the samples P1 to P4, an automated measuring program for the thermal analysis of the samples P1 to P4 can thus be carried out by means of the control and evaluation system 30 in such a way that the temperature control systems are controlled simultaneously for a step-by-step increase of the sample temperature according to a temperature program, which is input beforehand by a user, e.g., and such that the laser 18 for irradiating a first side of the respective sample is controlled by means of a predetermined electromagnetic excitation pulse at every temperature or temperature stage, respectively, which has been set in this way, and such that a signal provided by the detector 20 as a result of this irradiation is supplied to the control and evaluating system 30, in order to record corresponding measuring data in this way (which can specify the temperature-dependent course of the temperature conductivity of the individual samples P to P4, e.g., here).

At every temperature, which is adjusted during the course of the temperature program, all samples P1 to P4 can be consecutively subjected to a photothermal measurement by means of a corresponding control of the sample changing system 24, whereupon the control and evaluating system 30 controls the next temperature to be set by means of a corresponding control of the temperature control systems 16-1 to 16-4, and the procedure described above for this changed temperature is repeated etc., until an end temperature, which is defined by the temperature program, has been reached.

In response to a temperature control, which is accomplished by means of simultaneously controlling the individual temperature control systems 16-1 to 16-4, a regulation (based on the currently captured sample temperature) can advantageously be carried out, e.g., either a "proportional regulation" or (preferably) a more complex regulation (e.g. "PI" or "PID" regulation).

Figure 2:
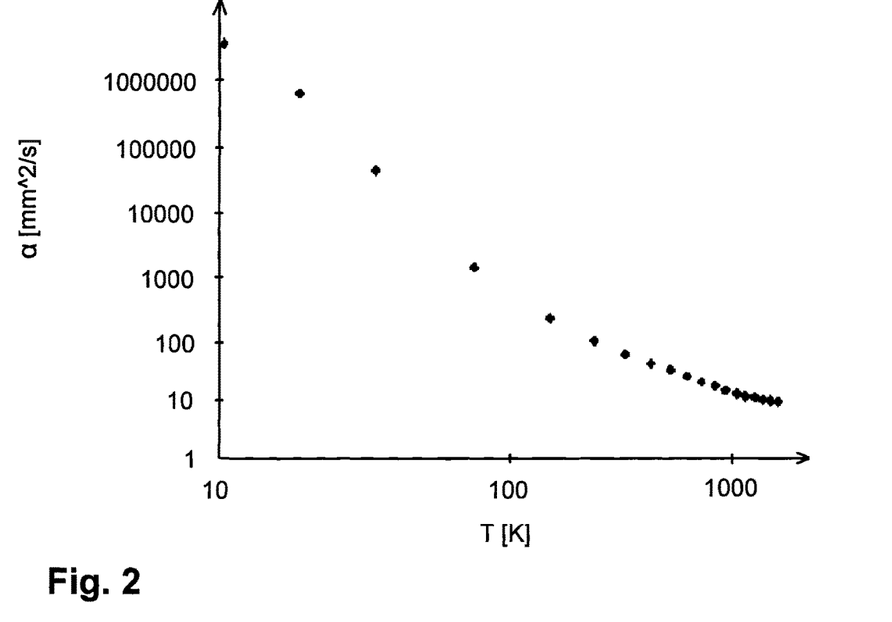
FIG. 2 shows an application of the temperature conductivity of silicon as a function of the temperature.

FIG. 2 shows the temperature conductivity a of a sample of silicon as a function of the sample temperature T as example of a physical property of a sample, which can be analyzed by means of the device 10.

It can be seen from this that the temperature conductivity a decreases strongly as the temperature T increases. In the illustrated range of between 10 K and 1,000 K, a decreases by approximately five magnitudes, for example. The photothermal measuring system of the device 10, which has already been described, allows the determination of such temperature-dependent courses of the temperature conductivity a of virtually any samples. Although such a determination of the thermal conductivity a as such is already known (so-called LFA ("Laser/Light Flash Analysis") method), this method will be discussed briefly by means of FIG. 3.

Figure 3:
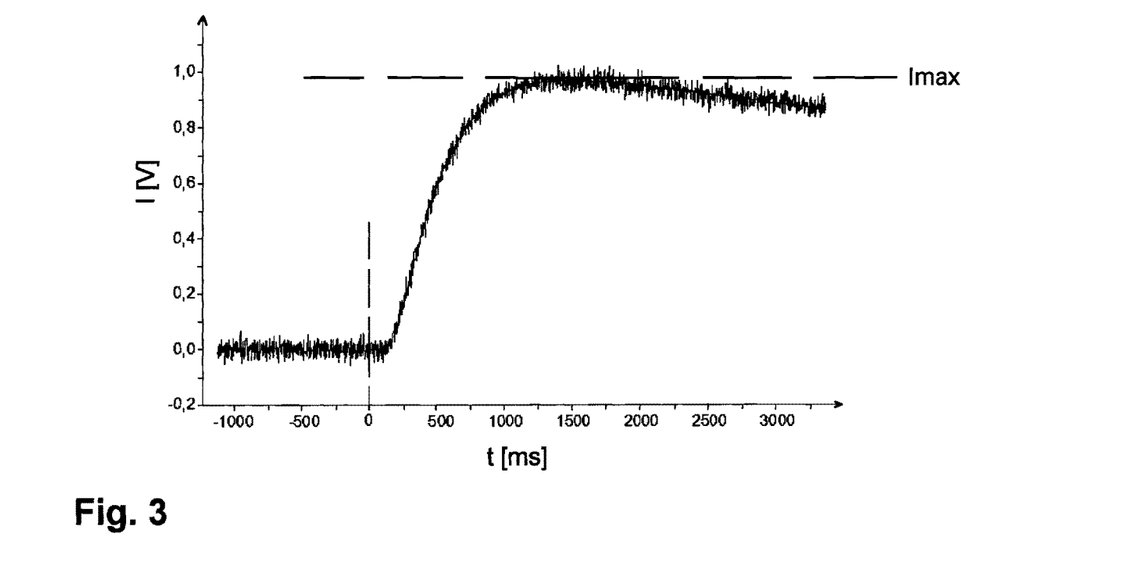
FIG. 3 shows a diagram of an exemplary course of a thermal radiation captured in response to a photothermal measurement on a sample as a function of the time.

For an opaque sample, FIG. 3 shows the chronological sequence, the chronological sequence if a detector signal I, which is representative for an intensity of the thermal radiation, which is captured by means of the detector 20, as a function of the time t.

For the sake of simplicity, it is assumed that the time-dependent course I(t), which is simultaneously representative for the chronological course of a temperature $T2(t)$ on the second side of the sample (facing the detector 20), will also be identified as "sample rear side" hereinafter.

Generally speaking, a corresponding conversion of the directly captured variable I(t) into a variable $T2(t)$, which may be required for a subsequent further evaluation, can always be carried out in a suitable manner by means of the control and evaluating system 30, with the knowledge of the properties of the detector 20 and of the amplification property of the signal amplifier 22, which is arranged downstream from the detector 20.

The irradiation of the first side of the sample (facing the laser 18), hereinafter also identified as "sample front side" of the sample, takes place in FIG. 3 at a point in time t=0, by means of a short excitation pulse of predetermined pulse energy and/or predetermined chronological sequence of a radiation current density (pulse duration e.g. approx. 10 µs).

In the case of an opaque sample, i.e. which is impermeably for thermal radiation, a heat input resulting from the irradiation on the sample front side corresponds to the integral of the radiation current density of the excitation pulse, which is multiplied by the irradiation surface, over the time t. In practice, the period of time (chronological "width") of the excitation pulse is mostly (and preferably) much shorter than that period of time, during which a temperature variation, which, depending on the sample thickness and sample properties (in particular, e.g. temperature conductivity a and thermal conductivity k) is characteristic, results subsequently on the sample rear side. It is sufficient in this case, when only the total energy of the excitation pulse (e.g. approx. 10 J) is known, e.g.

As can be seen from FIG. 3, a rise of the temperature or of the thermal radiation intensity I(t), respectively, starts at a period of time of approximately t=130 ms on the sample rear side. Concretely, this means that the thermal energy applied on the sample front side "arrives" at the sample rear side after approximately 130 ms.

At a point in time of approximately t=1,500 ms, the intensity I(t) runs through a maximum. Concretely, this means that more heat "is lost" into the environment on the sample rear side due to convection and/or radiation as of that point in time, than is (still) delivered subsequently through the sample interior by means of convection.

It is clear that the mentioned points in time, but also the entire detailed course of the thermal radiation intensity I(T) are in particular a function of the material parameters a and k and can be described by means of a suitable physical-mathematical model, so that the parameters a and k of the model can be readily estimated by means of a mathematical equalization calculus by means of the determined chronological sequence of the intensity I(t) (e.g. mathematical "fit" of the parameters a and k by means of the "least-squares method" or the like) and so that the material parameters thermal conductivity (k) and temperature conductivity (a) of the respective sample can thus be determined (calculated).

The control and evaluating system 30 can be equipped with (or connected to) suitable evaluating means (e.g. program-controlled processor unit) and display and/or storage means for outputting or storing, respectively, the determined material parameters.

The above-described method, including a physical-mathematical model, which is suitable for the evaluation, is described, e.g. in the patent publication DE 10 2012 106 955 A1.

In the context of the invention at hand, the photothermal measuring system provided at the device 10 and formed by the laser 18 and the detector 20 is only one example of a measuring system on the one hand, by means of which the measuring data, which are to be recorded for the "thermal analysis", are obtained, but, on the other hand, also a measuring system, which is mandatory in accordance with the invention (namely for calibrating the device 10), as it will become clear from the following description of the calibration.

In the illustrated exemplary embodiment, the temperature measurement (thermometry), which is required for recording the measuring data, is based on the sensor signals (e.g.: thermoelectric voltages), which are supplied to the control and evaluating system 30 by the temperature measuring sensors (e.g. thermocouples).

In practice, a more or less larger and systematic measuring error results on principle in response to this temperature measurement for each of the sample positions PA to PD in that the temperature measuring sensors 26-1 to 26-4 are not arranged in the respective sample P1, P2, P3 or P4, respectively, but adjacent thereto (here e.g. at the respective sample holder).

It is also significant in this context that unwanted temperature differences between the individual sample positions PA to PD can result in practice, e.g. due to unavoidable tolerances with respect to the production and arrangement of the sample holders 14-1 to 14-4 as well as of the assigned temperature control systems 16-1 to 16-4 (or other "asymmetries") even in the case of an identical simultaneous control of the temperature control systems 16-1 to 16-4, e.g. by means of a certain identical heating current intensity.

This is why the control and evaluating system 30 has a calibrating functionality, by means of which a "correction" of the temperature capturing and/or of the temperature control (in each case based on the mentioned correction parameters) is carried out by using corresponding "correction parameters" for the individual sample positions PA to PD.

A method for calibrating the temperature measuring system and/or the temperature control systems, which is provided in the case of the device 10, will be discussed below, which is understood as the determination and storing of the required correction parameters for the subsequent use in thermal analyses (in order to capture the sample temperature(s) more accurately or to provide the temperatures of the individual samples P1 to P4 identically, if possible, respectively).

This calibrating method comprises the following steps:
carrying out photothermal measurements by means of the photothermal measuring system (here: laser 18, detector 20, signal amplifier 22)
on a certain sample, which is consecutively held in the plurality of sample holders (here: 14-1 to 14-4) for this purpose and which is in each case subjected to a photothermal measurement, or
on a plurality of similar samples, which are in each case held in one of the plurality of sample holders (here: 14-1 to 14-4) and which are in each case subjected to a photothermal measurement,
wherein in the case of the photothermal measurements, a first side of the respective sample is in each case irradiated with an electromagnetic excitation pulse and a thermal radiation emitted by a second side of this sample located opposite the first side is captured as a result of the excitation pulse,
comparing results of the photothermal measurements for the plurality of sample holders (here: 14-1 to 14-4),
in each case determining at least one correction parameter for each sample holder (here: 14-1 to 14-4) or each sample position (here: PA to PD), respectively, based on a result of the comparison,
calibrating the temperature measuring system (here: temperature measuring sensors 26-1 to 26-4) and/or the temperature control systems (here: temperature control systems 16-1 to 16-4) based on the determined correction parameters.

In the illustrated exemplary embodiment, this calibrating method is advantageously provided in an automated manner insofar as the control and evaluating system 30 is embodied to carry out the following steps for carrying out the calibrating method:

controlling the sample changing system 24 of the device 10, in order to consecutively bring each of the sample holders 14-1 to 14-4 into a relative position, which is suitable for a photothermal measurement on a sample held therein (on the very left in FIG. 1), with regard to the photothermal measuring system, for each of the plurality of photothermal measurements:

controlling the respective temperature control system 16-1, 16-2, 16-3 or 16-4, respectively, for setting a predetermined temperature T of the respective sample and controlling the photothermal measuring system for irradiating the first side of the sample with a predetermined electromagnetic excitation pulse (preferably completely identical in the case of each photothermal measurement), measuring the temperature of the sample by means of the temperature measuring system 26-1 to 26-4, and recording measuring data (see, e.g., I(t) in FIG. 3), which represent a time-dependent course of the thermal radiation emitted by the second side of the sample, comparing results (measuring data) of the photothermal measurements for the plurality of sample holders 14-1 to 14-4, in each case determining at least one correction parameter for each sample holder 14-1 to 14-4, based on a result of the comparison, calibrating the temperature measuring system 26-1 to 26-4 (in combination with the control and evaluating system 30) and/or the temperature control systems 16-1 to 16-4 (in combination with the control and evaluating system 30), based on the determined correction parameters.

FIG. 4 shows once again the method steps, which are essential according to this example.

Figure 4:
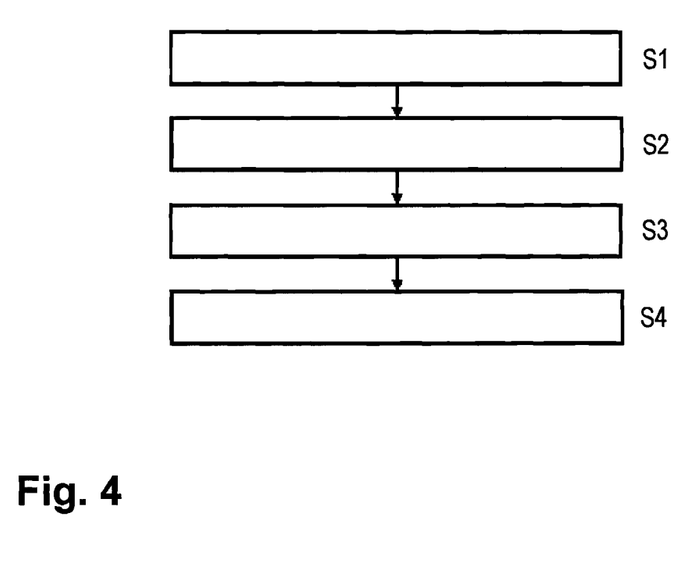
FIG. 4 shows a flow chart of a method for calibrating a device for the thermal analysis.

The photothermal measurements are carried out in a step S1.

The results of the photothermal measurements for the plurality of sample holders are compared to one another in a step S2.

Based on the result of the comparison, the correction parameters are determined for each sample holder in a step S3.

The actual calibration is carried out in a step S4, in that the correction parameters are stored in the control and evaluating system 30 and are considered accordingly in response to subsequent thermal analyses (in response to the temperature measurement or when controlling the temperature control devices 16-1 to 16-4, respectively.

In a particularly preferred embodiment, the comparison of the results of the photothermal measurements (step S2) comprises a comparison of the respective maximum values, which are in each case reached in a time-dependent course of the emitted thermal radiation (see, e.g., intensity I in FIG. 3).

Such a maximum value is illustrated and is identified with Imax in the example of FIG. 3.

In the ideal case, when carrying out the photothermal measurements on a certain sample or on a plurality of similar samples, in each case with identical electromagnetic excitation pulse, the maximum value Imax for all sample holders 14-1 to 14-4 or sample positions PA to PD, respectively, should be equal.

However, when differences between the individual measurements are determined in step S2 in this regard, these differences are used in step S3 to determine suitable correction parameters, so that the temperature capturing works more accurately and/or the temperature control of the individual samples (see, e.g. samples P1 to P4 in FIG. 1) is more even (in terms of a "uniform" or common sample temperature, respectively, for all samples), when considering these correction parameters in subsequent thermal analyses.

For this purpose, an example with regard to FIG. 1 once again:

Assuming that the temperature capturing system (26-1 to 26-4 in combination with 30) has already been calibrated otherwise with respect to the first sample holder 14-1 or the first sample position PA, respectively, e.g. in that the temperature of one or a plurality of "melting standards" (sample(s) comprising a known melting temperature) was controlled on the sample position PA and the sensor signal processing was adjusted in the control and evaluation system 30 by balancing the sample melting temperature(s) measured by the temperature measuring sensor 26-1 with the known melting temperature or temperatures, respectively, in such a manner that the sample temperature determined by means of the temperature measuring sensor 26-1 is "correct" (measured exactly).

The discussed photothermal measurements could then be carried out, e.g. for the same "calibrating temperature(s)" (or other calibrating temperatures, which serve as "support location", according to steps S1 and S2 for all sample positions PA to PD, and the results of these measurements could be compared to one another, wherein it shall be assumed below in an exemplary manner that the respective maximum values Imax, which are reached hereby in the time-dependent course of the emitted thermal radiation, are compared to one another.

It shall further be assumed in an exemplary manner that the maximum values Imax for the sample positions PA, PB and PC are in fact identical (for a certain calibrating temperature, which is measured exactly for the position PA and which is thus known), but that a deviation results for the last sample position PD, thus that a value of Imax is measured for the sample position PD, which is 1% larger, e.g., than the corresponding values for the sample positions PA, PB and PC.

However, when the value of Imax is larger for the sample position PD than the value for the sample position PA, this means that the sample measured at position PD has other properties than the sample measured (beforehand or simultaneously) at the position PA, which, in turn, can be explained in that the temperature of the sample at the position PD has in fact been controlled to a different temperature than the sample at the position PA.

In consideration of a (known) temperature dependence of the value of Imax from the sample temperature, the control and evaluating system 30 can hereby determine, whether the actual temperature at the position PD is smaller or larger than the temperature at the position PA, and possibly also how large exactly this temperature deviation is.

The control and evaluating system 30 can thus determine a "temperature control correction parameter" for the position PD in such a manner on this basis (or can update an already stored corresponding correction parameter in such a manner) that the control signal delivered to the temperature control system 16-4 at the used calibration temperature effects an improved adaptation of the temperature of position PD to the temperature of position PA.

The determination of the "temperature control correction parameter" for at least the sample positions, which have not already been calibrated otherwise beforehand (here, e.g. PB, PC and PD), can also be carried out iteratively, e.g. (by means of repeatedly carrying out the mentioned calibrating steps), and can also be carried out for a plurality of different calibrating temperatures, which can serve as "support locations" for a temperature-dependent course of the correction parameters, which is to be determined and which is supplemented by means of an interpolation, e.g., between the support locations.

For example (and advantageously) after such a calibration of the temperature control, a calibrating of the temperature capturing can be carried out as well in that the temperature capturing for the sample position PA, which is to be assumed as being "exact" in the example, is used as basis for this, in order to assess the temperatures captured for the remaining positions, here PB, PC and PD, by means of evaluation, to what extent a correction of the temperature capturing is required for these remaining positions PB, PC and PD.

For this purpose, the control and evaluating system 30 can in each case determine a "temperature capturing correction parameter" for the positions PB, PC and PD in such a way (or can update an already stored corresponding correction parameter in such a way) that the temperatures captured in a corrected manner for the positions PB, PC and PD in the case of the used calibrating temperature correspond to the temperature captured for position PA.

The determination of the "temperature capturing correction parameters" for the respective sample positions (here PB, PC and PD) can advantageously also be carried out for a plurality of different calibrating temperatures, which can serve as "support locations" of a temperature-dependent course of the correction parameters, which is to be determined and which is defined between the support locations, e.g. by means of an interpolation.

If the temperature control as well as the temperature capturing were calibrated, the temperature control is homogenized in the subsequent thermal analyses (by means of the improved adjustment of the heating power ratios between the individual temperature control systems 16-1 to 16-4) and the accuracy of the temperature measurement is increased (here, e.g. by means of a "corrected" conversion of the signals supplied by the temperature measuring sensors 26-1 to 26-4 into corresponding temperature information).

In summary, it is made possible in the case of the calibration of the device 10 according to the invention to calibrate the temperature measuring system and/or the temperature control systems thereof. If applicable, an iterative process can be carried out hereby, until it is determined on the one hand by means of the values of Imax that the same sample temperature is in fact reached for all positions PA to PD in response to the temperature control (which can be recognized by means of identical values of Imax) and, on the other hand, until all sample temperatures determined for the positions PA to PD by means of the temperature measuring sensors 26-1 to 26-4 are identical. It is particularly advantageous hereby, when a calibration of the temperature capturing, which is realized otherwise, e.g. has already been carried out prior to the described calibrating steps for one of the plurality of sample holders 12-1 to 12-4. An "adjustment of the remaining sample holders" (to the previously calibrated sample holder) can quasi be accomplished in this case by means of the calibrating steps.

In particular in the case of a device for the thermal analysis, in the case of which the analysis is provided across a larger temperature range, the described calibrating method should be carried out for a plurality of sample temperatures ("calibrating temperatures"), which serves as "support points across this temperature range", in order to reach the calibration of the temperature measuring system and/or of the temperature control systems not only for a certain temperature, but for a plurality of "calibrating temperatures" accordingly.

What is claimed is:

1. A method for calibrating a device for the thermal analysis including:
   a sample chamber comprising a plurality of sample holders, each sample holder embodied to hold a sample,
   for each of the plurality of sample holders, a temperature control system assigned to each said sample holder, for controlling the temperature of the sample held by this sample holder,
   a temperature measuring system for measuring the temperature of the samples,
   a photothermal measuring system for irradiating a first side of the samples comprising an electromagnetic excitation pulse and for capturing a thermal radiation emitted by a second side of the samples located opposite the first side as a result of the excitation pulse,
   a control and evaluating system for controlling each temperature control systems and the photothermal measuring system and for recording measuring data, which represent at least one physical property of the samples, which differs from the temperature of the samples, as a function of the temperature of the samples, wherein the method for calibrating comprises:
   carrying out photothermal measurements by the photothermal measuring system
      on a certain sample, which is consecutively held in the plurality of sample holders for this purpose and which subjected to a photothermal measurement, or
      on a plurality of similar samples, which are held in one of the plurality of sample holders for this purpose and which subjected to a photothermal measurement,
   wherein in the photothermal measurements, a first side of the respective sample is irradiated with an electromagnetic excitation pulse and a thermal radiation emitted by a second side of this sample located opposite the first side is captured as a result of the excitation pulse,
   comparing results of the photothermal measurements for the plurality of sample holders,
   determining at least one correction parameter for each sample holder based on a result of the comparison,
   calibrating the temperature measuring system and/or the temperature control systems based on the determined correction parameters.

2. The method according to claim 1, wherein the device further comprises a controllable sample changing system, by which each of the sample holders is brought into a relative position, which is suitable for a photothermal measurement on a sample held herein, with regard to the photothermal measuring system.

3. The method according to claim 1, wherein each temperature control system has an electrically operable heating jacket, which is arranged on the assigned sample holder.

4. The method according to claim 1, wherein each temperature measuring system has a temperature sensor, which is arranged in the sample chamber and which is shared by the plurality of sample holders.

5. The method according to claim 1, wherein the temperature measuring system for each sample holder has an assigned temperature measuring sensor, which is arranged in the sample chamber.

6. The method according to claim 1, wherein the control and evaluating system is embodied to carry out the following steps for carrying out the calibrating method:
controlling the respective temperature control system for setting a predetermined temperature of the respective sample,
measuring the temperature of each sample by the temperature measuring system and
recording measuring data, which represent a time-dependent course of the thermal radiation emitted by the second side of each sample,
comparing results of the temperature measurements for the plurality of sample holders,
using the compared results of the temperature measurements as part of determining at least one correction parameter for each sample holder.

7. The method according to claim 1, wherein the comparing of the results of the photothermal measurements comprises a comparison of the respective maximum values (Imax) reached in the time-dependent course of the emitted thermal radiation.

8. The method according to claim 2, wherein each temperature control system has an electrically operable heating jacket, which is arranged on the assigned sample holder.

9. The method according to claim 2, wherein the temperature measuring system has a temperature sensor, which is arranged in the sample chamber and which is shared by the plurality of sample holders.

10. The method according to claim 2, wherein the temperature measuring system for each sample holder has an assigned temperature measuring sensor, which is arranged in the sample chamber.

11. The method according to claim 2, wherein the control and evaluating system is embodied to carry out the following steps for carrying out the calibrating method:
controlling the respective temperature control system for setting a predetermined temperature of the respective sample,
measuring the temperature of the sample by means of the temperature measuring system and
recording measuring data, which represent a time-dependent course of the thermal radiation emitted by the second side of the sample,
comparing results of the temperature measurements for the plurality of sample holders,
using the compared results of the temperature measurements as part of determining at least one correction parameter for each sample holder.

12. The method according to claim 2, wherein the comparing of the results of the photothermal measurements comprises a comparison of the respective maximum values (Imax) reached in the time-dependent course of the emitted thermal radiation.

13. The method of claim 6, further comprising:
controlling a sample changing system of the device, in order to consecutively bring each of the sample holders into a relative position, which is suitable for a photothermal measurement on a sample held therein, with regard to the photothermal measuring system.

14. The method of claim 11, further comprising:
controlling a sample changing system of the device, in order to consecutively bring each of the sample holders into a relative position, which is suitable for a photothermal measurement on a sample held therein, with regard to the photothermal measuring system.

* * * * *